United States Patent [19]

Martell

[11] 4,448,206
[45] May 15, 1984

[54] VENTED, ASPIRATING SYRINGE

[76] Inventor: Michael D. Martell, 7555 Jurupa Ave., #E, Riverside, Calif. 92504

[21] Appl. No.: 449,560

[22] Filed: Dec. 13, 1982

Related U.S. Application Data

[63] Continuation-in-part of Ser. No. 293,662, Aug. 17, 1981, Pat. No. 4,373,535.

[51] Int. Cl.³ .............................................. A61B 5/00
[52] U.S. Cl. .................................... 128/765; 604/190
[58] Field of Search ............... 128/765, 766; 604/190, 604/222, 405, 406

[56] References Cited

U.S. PATENT DOCUMENTS

| | | | |
|---|---|---|---|
| 1,363,128 | 12/1920 | Kitaoka | 604/190 |
| 3,669,111 | 6/1972 | Dubner | 128/218 |
| 3,766,917 | 10/1973 | Wimmer | 128/218 |
| 3,910,273 | 10/1975 | Arlers | 128/218 |
| 4,257,426 | 3/1981 | Bailey | 128/766 |
| 4,266,557 | 5/1981 | Merry | 604/222 |
| 4,327,745 | 5/1982 | Ford, Jr. | 128/765 |

Primary Examiner—John D. Yasko
Attorney, Agent, or Firm—Gausewitz, Carr, Rothenberg & Edwards

[57] ABSTRACT

A syringe comprises a main tubular body, the body being open at one end and receiving a hypodermic needle at the other end, and a plunger, one end of the plunger extending into the body, through the open end thereof, the plunger having a longitudinal passageway therein permitting air flow therethrough. A fluid-tight seal is formed between the outside surface of the plunger and the inside surface of the syringe body. An air permeable filter member extends across the first end of the plunger, in the passageway, whereby the body can fill with blood, causing the air in the body to pass through the filter member to the open end of the body. The blood does not flow through the filter. A valve extends across the passageway and allows the syringe to be used to aspirate in the absence of natural blood pressure.

17 Claims, 4 Drawing Figures

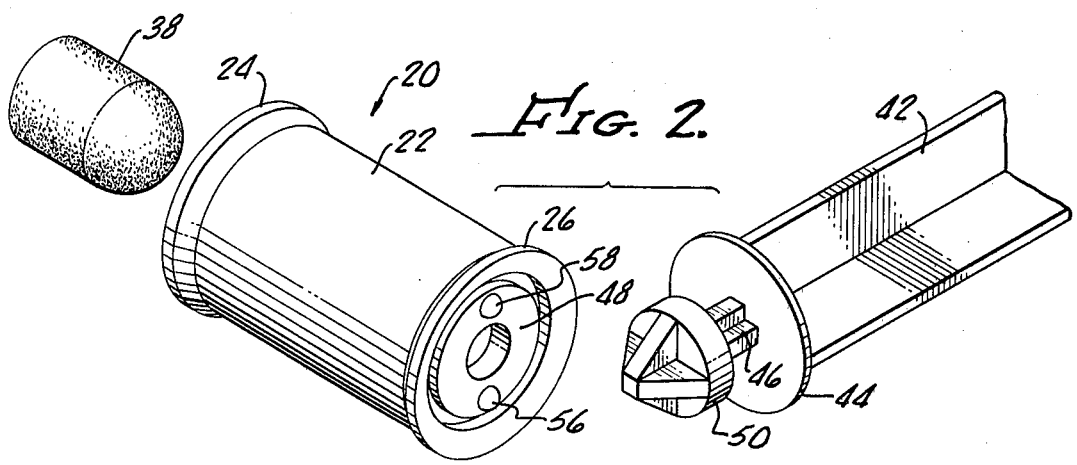
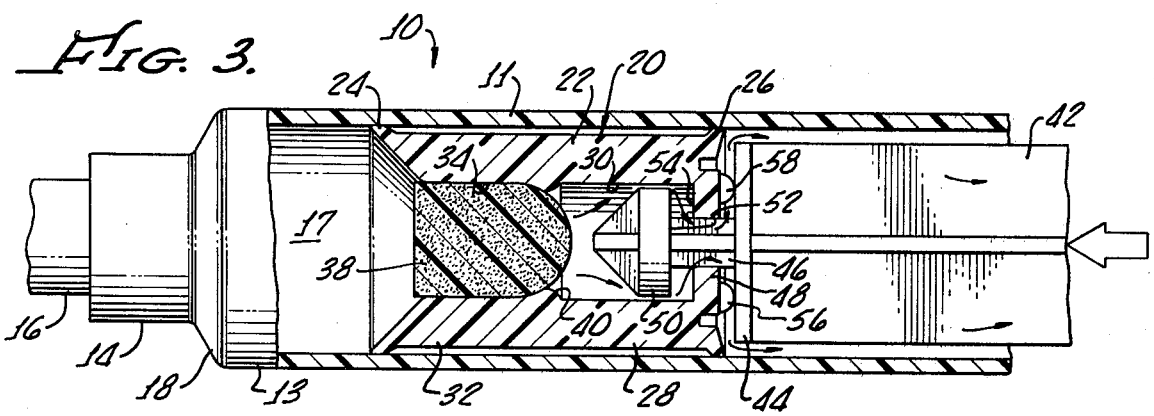
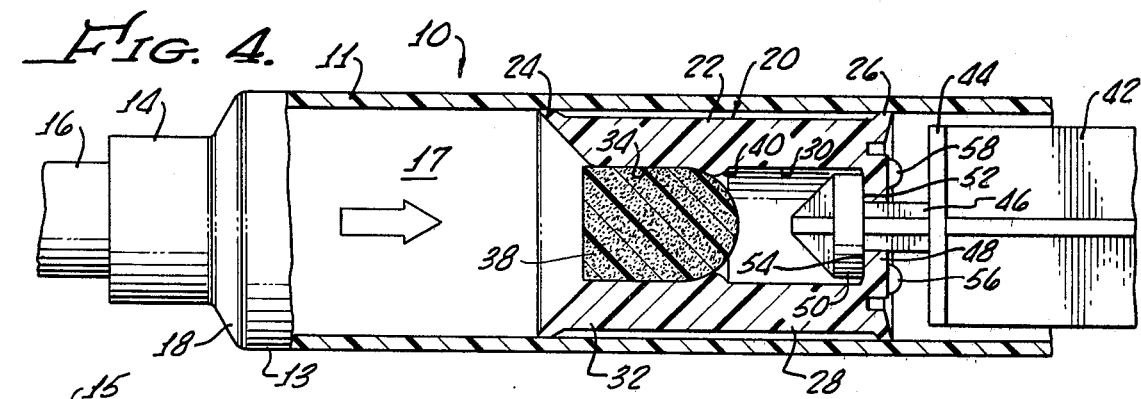
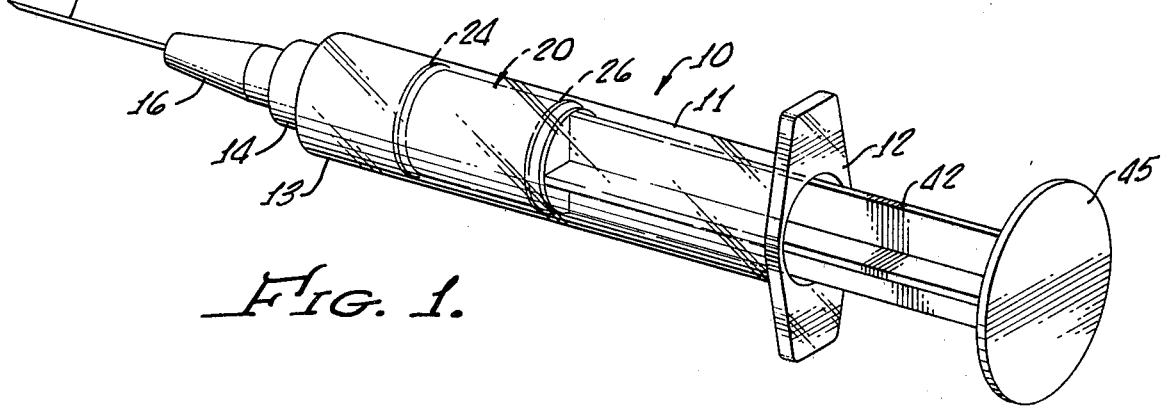

VENTED, ASPIRATING SYRINGE

CROSS-REFERENCE TO RELATED APPLICATION

This application is a continuation-in-part of U.S. application Ser. No. 293,662, filed Aug. 17, 1981 now U.S. Pat. No. 4,373,535 for a Venting, Self-Stopping, Aspirating Syringe, the disclosure of which is incorporated herein by this reference as though fully set forth.

BACKGROUND OF THE INVENTION

The present invention relates to a vented, aspirating syringe and, more particularly, to a syringe which does not require a timely withdrawal of the syringe from an artery, and which minimizes blood air interface during the obtaining of the blood sample.

DESCRIPTION OF PRIOR ART

Syringe type devices are typically used for obtaining blood samples to perform a blood gas analysis. Many such blood gas analyses require the drawing of arterial blood which has a sufficient pressure whereby it will, in and of itself, under normal circumstances, fill a syringe without the necessity of aspirating. For this purpose, a conventional syringe type device simply consists of a plunger positioned within a main tubular body. The plunger is fully inserted into the main tubular body and the hypodermic needle punctures the artery. As blood flows into the syringe body, the plunger is pushed back thereby.

There are a variety of problems associated with the use of such a conventional syringe. First of all, it is necessary to draw heparin (an anti-coagulant) into the tubular syringe body through the hypodermic needle which exposes the needle to possible contamination. This anti-coagulant is necessary to maintain the integrity of the blood sample. Furthermore, when the plunger is pushed into the syringe body to expel the excess liquid heparin, a small quantity, approximately ¼ cc, remains in the syringe, in the area between the end of the plunger and the tip of the hypodermic needle. Therefore, when such a syringe is used to obtain a blood sample to perform a blood gas analysis, the ¼ cc of liquid heparin remains in the syringe. This small amount of heparin represents a diluent which interferes with accurate blood gas analysis values and other chemical evaluations.

As a result of the above problems in the use of conventional syringes for obtaining blood samples to perform a blood gas analysis, several syringe devices have been developed to obtain diluent-free blood samples. An example of such a device is shown in U.S. Pat. No. 4,257,426 to Bailey. In the Bailey patent, a syringe device includes a main tubular body, one end of which slidably receives a combination sealing member and hollow plunger, with the plunger being rotatably connected to the sealing member. The sealing member has several circular lips so that contact, sufficient to create a seal, exists between the lips on the sealing member and the syringe body. The sealing member has a lateral vent between several of the lips. A flexible thread fixed to the plunger selectively crosses the lips and breaches the seal created by the sealing member to establish communication between the interior of the plunger and the interior of the tubular body via the lateral vent in the sealing member. Removal of the thread allows a seal to be restored so that a gas-free blood sample can be isolated in the hollow tubular body. Crystalline heparin is placed in the body, eliminating the need for liquid heparin.

The Bailey syringe has a variety of advantages over a conventional syringe. Initially, through the use of crystalline heparin, the use of liquid heparin can be eliminated, making blood gas analyses more accurate. Secondly, because of the venting action of the plunger, the blood can rush into the syringe body, pushing the air across the lips and around the flexible thread. As soon as the blood passes the first series of lips, the syringe is removed from the patient and the plunger is rotated, removing the thread from the seal lips, restoring the seal so that the blood sample can be isolated in the hollow tubular body.

While the syringe of the Bailey patent solves some problems associated with conventional syringes, it creates a new set of problems. That is, since the flexible thread extends across the seal lips and breaches the seal created by the sealing member, blood, as well as air, can flow past the sealing member. Accordingly, proper operation of the device requires removal of the needle at a precise time from the patient. If the syringe is not removed at the precisely correct time, the blood flows past the sealing member and enters the syringe body, on the backside of the sealing member. Then, when the syringe is removed and inverted, this blood escapes. Furthermore, since the plunger must be preset to the desired volume of blood to be drawn, a blood-air interface is created, resulting in a possible air contamination to the arterial sample which wille affect the blood gas values.

The use of the syringe of the Bailey patent also requires the technician to learn an entirely new procedure, that of rotating the plunger relative to the sealing member to withdraw the thread. In view of the number of technicians which draw blood, this additional training to use the product properly is a significant disadvantage, especially when the operation of the device is not at all apparent from an inspection thereof.

SUMMARY OF THE INVENTION

According to the present invention, there is provided a syringe which solves these problems in a manner unknown heretofore. The present syringe does not require a technician to watch the blood carefully as it moves through the syringe body to prevent spilling into the back of the tubular body, behind the plunger. Still further, the present syringe does not require any additional step, such as the rotation of one member relative to another, as in the syringe of the Bailey patent. Once the flow of blood comes into contact with the filter member, the blood is automatically sealed from air within the hollow tubular body.

The present syringe also permits the use of dry-flake heparin so that the problems associated with liquid heparin are also eliminated. Finally, the present syringe can be used in an aspirating mode in those situations where individuals have insufficient blood pressure to fill the body of the syringe without having to manipulate the plunger.

Briefly, the present syringe comprises a main tubular body being open at one end thereof and being adapted to receive a hypodermic needle at the other end thereof; a plunger, one end of the plunger being extendable into the body, through the open end thereof, the plunger having a longitudinal passageway therein permitting air flow therethrough; means forming a fluid-tight seal between the outside surface of the plunger and the inside surface of the body; an air permeable filter member extending across the first end of the plunger, in the passageway; and a valve extending across the passageway, between the filter member and the open end of the body, the valve being selectively operable to open or closed positions and preventing passage of air through the passageway in either direction when closed. The valve is manually controlled and automatically closes when the syringe handle is pulled, as when used in an aspirating mode.

OBJECTS, FEATURES AND ADVANTAGES

It is, therefore, an object of the present invention to solve the problems encountered heretofore in providing a syringe device for taking blood samples. It is a feature of the present invention to solve these problems by providing a syringe device including a plunger having a passageway therein and an air permeable filter member and a valve extending across the passageway. An advantage to be derived is a syringe in which dry flake heparin can be used. A further advantage is a free venting syringe. Another advantage is a syringe which does not permit blood leakage. Still another advantage is a syringe in which no additional steps are needed to prepare the syringe for aspiration. Another advantage is a syringe which requires no additional training for the use thereof. An additional advantage is a syringe which can be used both for obtaining arterial blood and in an aspirating mode.

Still other objects, features, and attendant advantages of the present invention will become apparent to those skilled in the art from a reading of the following detailed description of the preferred embodiments constructed in accordance therewith, taken in conjunction with the accompanying drawings wherein like numerals designate like or corresponding parts in the several figures.

BRIEF DESCRIPTION OF THE DRAWINGS

FIG. 1 is a perspective view of a syringe constructed in accordance with teachings of the present invention;

FIG. 2 is an exploded perspective view of the syringe plunger;

FIG. 3 illustrates the syringe plunger of FIG. 2 with its valve in open position; and, FIG. 4 illustrates the plunger of FIG. 2 with its valve in closed condition.

DETAILED DESCRIPTION

Referring now to the drawings, one form of syringe, generally designated 10, includes a transparent or translucent main tubular body 11 of circular transverse section having an open end 12 and a closed end 13 having a neck 14 which protrudes axially from end 13. A hypodermic needle 15 is frictionally connected to or screwed onto neck 14 by a needle hub 16. Neck 14 is hollow and communicates with an interior chamber 17 generally defined by the space in tubular body 11, the end wall 18 of body 11 and a hollow plunger, generally designated 20, which is received in tubular body 11, through open end 12 thereof.

The plunger includes a tubular, soft rubbery plastic sealing cylinder 22 having flexible frustoconical sealing elements 24 and 26 respectively projecting axially and outwardly from the cylinder body into engagement with the interior of the main tubular syringe body 10.

The tubular body 22 has a rear portion 28, adjacent the open end of the syringe body 10, formed with a relatively large diameter bore 30 and a forward portion 32 formed with a relatively smaller diameter bore 34.

A filter member 38 is formed of a relatively hard cylindrical air permeable porous plug 38 that is inserted into the relatively small diameter bore portion 34, outwardly compressing the soft material of the sealing cylinder body 22 to form a shoulder 40. By means of its inherent resilience, the sealing cylinder body firmly retains the porous filter plug 38 within its bore. The filter plug is preferably formed of a porous polyethylene that readily permits passage of air but which will present passage of blood.

The main portion of the plunger body is formed by a hard plastic rod which provides an elongated handle 42. The handle, for a major portion of its length, has a generally cross-shaped cross-section and has a flat transverse disc 44 adjacent a forward portion of the handle and which terminates in an enlarged head 45 at its rearward end. A smaller diameter handle section or handle neck 46 extends forwardly from the handle disc 44 and through a centrally located aperture in an end cap 48 that is formed at the rear end of the tubular sealing cylinder 22. The smaller diameter handle portion 46 terminates in an enlarged forward end or nipple 50 having a rearwardly facing flat surface 52 which is adapted to cooperate with a flat, forwardly facing interior face 54 of the end cap 50 to seal the interior passageway of the tubular sealing cylinder 22. The outer or rearwardly facing surface of end cap 48 is formed with a plurality of rearwardly projecting protrusions 56, 58 that are adapted to engage a forwardly facing surface of the handle disc 44 and prevent the latter from moving into sealing engagement with the outer surface of end cap 50.

The tubular sealing cylinder 22 is made of a soft rubbery plastic material such as, for example, a material known under the trademark KRATON thermoplastic rubber which comprises a mixture containing styrene ethylene/butylenestyrene block copolymer, polypropylene, process oil, filler, plus minor amounts of antioxidant/stabilizer and dusting agent, made by Shell under the name KRATON G7705-1001-1 Thermoplastic Rubber. The material is relatively soft, having a shore hardness of about 45, whereas the plunger is made of a rigid, considerably harder, material having a shore hardness of in excess of 250. The rod handle may be a rigid polypropylene, for example. It is preferred to employ a cylindrical filter plug made of a porous polyethylene and having a hardness considerably greater than that of the KRATON material of the tubular sealing cylinder. As previously mentioned, the filter plug permits passage of air but not blood.

The length of the intermediate reduced diameter handle section 46 is greater than the sum of the thickness of sealing cylinder end cap 48 and its protrusions 56, 58, so that, when the handle is pushed toward the sealing cylinder and the entire plunger then is moved forwardly, toward the left as viewed in FIGS. 3 and 4, sealing surface 52 of handle end 50 is displaced from the mating sealing surface 46 of the interior surface of end cap 48. Thus, as the reduced handle section 46 is also of a cross-shaped cross-section, and the diameter of handle end 50 handle is less than the diameter of the bore 30 of cylinder 22, the valve is opened and air may pass from the interior of syringe body 10 through the porous plug 38 and through the valve.

However, when the syringe is used in an aspirating mode, and the handle is pulled to the right (as viewed in FIGS. 3 and 4) so as to start withdrawal of the plunger from the syringe body, the lost motion connection between the handle section and the sealing cylinder allows the enlarged end 50 of the handle to move rearwardly relative to the tubular sealing cylinder until its rearwardly facing surface 52 abuts the interior surface 54 of the tubular sealing cylinder end cap 48 to thereby seal the valve. Accordingly, as the handle is manipulated to start retraction of the plunger, the valve automatically closes to seal the interior of the plunger sealing cylinder 22 and prevent air from passing through its passageway. This permits a syringe that is fitted with the plunger assembly of FIGS. 2, 3 and 4 to be used in either an aspirating mode or to obtain arterial blood samples.

For use in drawing an arterial blood sample, the forward end 32 of the plunger is pushed forwardly against the forward end 18 of the tubular body and the needle is inserted into an artery from which a blood sample is to be taken. Normal pressure of the arterial blood then forces the blood into the syringe, between the forward end 32 of the tubular sealing cylinder and the forward end 18 of the syringe body, driving the air out of the body through the porous plug 38 and through the open valve formed by the interengaging parts of the handle and sealing cylinder. When the blood contacts the filter member after evacuating all air out of the dead space between end wall 18 and filter member 38, the pressure of the blood causes the plunger assembly to move back into the tubular body 11, from left to right as viewed in FIGS. 3 and 4. This action will occur under arterial pressure above twenty millimeters of mercury. Blood air interface is minimized during the taking of a blood sample because the procedure is started with the plunger pushed forwardly to a position in which there is a minimum volume of air within the syringe body. Moreover, this small amount of air is rapidly discharged through the porous plug and, therefore, a minimum contact between blood and air within the syringe occurs during the remainder of the blood withdrawal.

The unique sealing elements 24 and 26 eliminate the need for separate O-rings and, moreover, provide effective sealing with a considerably decreased frictional resistance to sliding motion of the sealing cylinder along the interior surface of the syringe cylinder. Because of the axially projecting configuration of the frustoconical sealing elements, each will operate to seal primarily in only one direction. For example, as the plunger assembly is moved to the left, as viewed in FIG. 3, the rearward sealing element 26 tends to move in a direction in which it creates a lesser resistance because this direction of motion tends to move the outwardly projecting conical element 26 radially inwardly. The same direction of motion, toward the left as viewed in FIGS. 3 and 4, causes the frustoconical sealing element 24 to exert a maximum sealing contact because this direction of relative motion tends to bend the element 24 outwardly, creating an increased sealing contact. The same is true in the reverse, for motion of the plunger in the opposite direction, which is toward the right as viewed in FIGS. 3 and 4. With such motion, the sealing element 24 produces relatively little frictional resistance as it tends to collapse, whereas the sealing element 26 tends to increase its sealing contact with this motion.

To use the plunger assembly of FIGS. 3, and 4 in an aspirating mode, the plunger assembly is moved to the left to drive the plunger deeper into the syringe body, as illustrated in FIG. 3. During this motion, air trapped between the forward end of the sealing cylinder and the closed end of the plunger body, flows outwardly through the pores of sealing member 38 and through the valve which is open, having the handle disc 44 pressing against the end cap projections 56, 58.

When the handle is moved toward the right so as to tend to withdraw the plunger from the syringe body, the relatively hard enlarged handle end 50 moves to abut the relatively soft end cap 48 of the sealing cylinder, closing the valve automatically upon such motion and sealing the interior of the syringe.

It can therefore be seen that according to the present invention, there is provided a syringe which solves the problems encountered heretofore in a unique and unobvious manner.

The syringe also permits the use of dry heparin so that the problems associated with liquid heparin are also eliminated. A flake of heparin, prepared in any known manner, may be placed in a dried state within chamber 17 so that any blood received is immediately exposed to the heparin. The heparin flakes (not shown) can be stored along with the syringe for immediate use.

In addition, the syringe can be used in an aspirating mode in those situations where individuals have insufficient blood pressure to fill the body of the syringe.

The unique valve enables the syringe to operate either for withdrawal of arterial blood under its own pressure, or in an aspirating mode. The valve operates automatically as an automatically controlled manual valve. The unique integral formation of frustoconical sealing elements on the relatively soft and resilient tubular sealing cylinder of the plunger provides a simplified, inexpensive and more effective and more efficient seal.

Although the invention has been described with respect to a preferred physical embodiment constructed in accordance therewith, it will be apparent to those skilled in the art that various modifications and improvements may be made without departing from the scope of the invention. Accordingly, it is to be understood that the invention is not to be limited by the specific illustrative embodiments, but only by the scope of the appended claims.

What is claimed is:

1. A syringe assembly comprising:
   a tubular body open at one end and being adapted to receive a hypodermic needle at the other end thereof;
   a plunger, one end of which is adapted for insertion into said tubular body through said open end, said plunger having a longitudinal passageway for air flow therethrough;
   means for forming a fluid-tight seal between the outside surface of said plunger and the inside surface of said tubular body; an air permeable filter member extending across said passageway adjacent said one end of said plunger;
   a handle movably connected to the plunger to move the plunger within said tubular body; and
   said handle and plunger having mutually interengaging means forming valve means extending across said passageway between said filter member and said open end of said tubular body for selectively permitting the passage of air through said passageway, said valve means including relatively movable parts on said handle and plunger.

2. The syringe assembly of claim 1, wherein said plunger comprises a tubular sealing cylinder having said filter member mounted thereon, said mutually engaging means forming said valve means being positioned within said cylinder and operable to block passage of air through said passageway when said handle is pulled toward said open end of said tubular body.

3. A syringe assembly comprising:
a tubular body open at one end and being adapted to receive a hypodermic needle at the other end thereof;
a plunger, one end of which is adapted for insertion into said tubular body through said open end, said plunger having a longitudinal passageway for air flow therethrough;
means for forming a fluid-tight seal between the outside surface of said plunger and the inside surface of said tubular body; an air permeable filter member extending across said passageway adjacent said one end of said plunger;
a handle connected to move the plunger within said tubular body; and said handle and plunger having mutually interengaging means forming valve means extending across said passageway between said filter member and said open end of sad tubular body for selectively permitting the passage of air through said passageway, said plunger (comprises) comprising a sealing cylinder,
said cylinder having an apertured end cap,
said handle extending through the aperture of said end cap and having an enlarged end captured within said sealing cylinder,
said end cap and enlarged handle end forming said valve means.

4. The syringe assembly of claim 3, wherein said end cap and enlarged handle end have mutually mating surfaces adapted to seal against one another when said handle is pulled toward said open end of said tubular body, and means for preventing said handle from sealing against the surface of said end cap that faces toward said open end of said tubular body.

5. The syringe assembly of claim 1, wherein said plunger comprises a tubular sealing cylinder, said seal forming means comprising first and second sealing elements at opposite ends of said sealing cylinder, each said sealing element comprising a frustoconical ring projecting axially and outwardly from a respective one of the sealing cylinder ends into engagement with the interior surface of tubular body, whereby each sealing element effectively seals between the tubular body and the sealing cylinder primarily in only one direction of motion of the sealing cylinder relative to the tubular body.

6. A syringe assembly as recited in claim 1, wherein said seal forming means is positioned adjacent said one end of said plunger.

7. A syringe assembly as recited in claim 1, wherein said filter member comprises a porous cylindrical plug.

8. A syringe assembly as recited in claim 1, wherein said valve means prevents the passage of air through said passageway in either direction.

9. A plunger for use with a conventional syringe comprising:
an elongated body having a longitudinal passageway therein for permitting air flow therethrough;
an air permeable filter member extending across said passageway adjacent one end of said body;
an elongated handle movably mounted to said body; and
said body and handle having mutually interengaging means forming valve means extending across said passageway between said member and the other end of said body for selectively permitting the passage of air through said passageway, said mutually interengaging means comprising a first valve part on said body and a second valve part on said handle, said valve parts being movable to and from engagement with one another in response to motion of the handle.

10. A plunger for use with a conventional syringe comprising:
an elongated body having a longitudinal passageway therein for permitting air flow therethrough;
an air permeable filter member extending across said passageway adjacent one end of said body;
an elongated handle; and
said body and handle having mutually interengaging means forming valve means extending across said passageway between said member and the other end of said body for selectively permitting the passage of air through said passageway,
said body having an apertured end cap,
said handle extending through the aperture of said end cap and having
an enlarged end captured within said body,
said end cap and enlarged handle end forming said valve means.

11. The plunger of claim 10, wherein said end cap and enlarged end have mutually mating surfaces adapted to seal against one another when the handle is pulled away from said one end of said body and including means for preventing the handle from sealing against an external surface of said end cap.

12. The plunger of claim 9, wherein said body includes first and second sealing elements at opposite ends thereof, each said sealing element comprising a frustoconical ring projecting axially and outwardly from a respective one of the elongated body ends, whereby each sealing element effectively seals primarily in only one direction of motion of the elongated body when the body is inserted into a tubular syringe body.

13. The plunger of claim 12 wherein said sealing elements are integral with said body and all are formed of a relatively soft resilient material, said handle member being formed of a relatively harder and more rigid material.

14. A plunger as recited in claim 9, wherein said one end of said elongated body comprises a resilient material which is adapted to engage the inside surface of a conventional tubular syringe body to provide said seal forming means.

15. A plunger as recited in claim 14, wherein said filter member is formed of a porous polyethylene material.

16. A plunger as recited in claim 14 wherein said filter member comprises a porous cylindrical plug made of polyethylene.

17. A plunger as recited in claim 14, wherein said valve means prevents passage of air through said passageway in either direction.

* * * * *

UNITED STATES PATENT AND TRADEMARK OFFICE
CERTIFICATE OF CORRECTION

PATENT NO. : 4,448,206
DATED : May 15, 1984
INVENTOR(S) : Michael D. Martell

It is certified that error appears in the above-identified patent and that said Letters Patent are hereby corrected as shown below:

Column 6, line 55, and Column 7, line 16, there should be a paragraph following "body;" and before "an air permeable".

Column 7, line 25, delete "(comprises)".

Column 8, lines 26 and 27, there should be no paragraph between "and having" and "an enlarged".

Signed and Sealed this

Eighteenth Day of September 1984

[SEAL]

Attest:

GERALD J. MOSSINGHOFF

Attesting Officer

Commissioner of Patents and Trademarks